United States Patent [19]

Collmann

[11] 4,449,226
[45] May 15, 1984

[54] VEHICLE WHEEL TESTING OR INSPECTION SYSTEMS

[76] Inventor: Wilhelm Collmann, Auf der Höhe 25, 2400 Lübeck, Fed. Rep. of Germany

[21] Appl. No.: 367,424

[22] Filed: Apr. 12, 1982

[30] Foreign Application Priority Data

Apr. 18, 1981 [DE] Fed. Rep. of Germany ....... 3115735

[51] Int. Cl.³ ............................................. G03B 41/16
[52] U.S. Cl. ......................................... 378/58; 378/61
[58] Field of Search ................................... 378/58, 61

[56] References Cited

U.S. PATENT DOCUMENTS

3,852,600 12/1974 Faulkner ............................... 378/61
3,903,416 9/1975 Fox ....................................... 378/61

*Primary Examiner*—Craig E. Church
*Attorney, Agent, or Firm*—Balogh, Osann, Kramer, Dvorak, Genova & Traub

[57] ABSTRACT

This invention relates to inspection or X-ray testing system for vehicle wheels consisting of a rim and a supporting structure of the kind comprising an X-ray tube, and X-ray screen with a post-positioned monitor and a system for reception of the wheel fed in rim-down, for placing the same into the beam path of the X-ray tube, and for ejecting the wheel after inspection. To shorten the inspection or testing period, the system according to the invention comprises a chute displaceable around a horizontal pivot spindle for the wheel which may be pivoted to the appropriate positions for reception, immobilization during the testing or inspection and the ejection of the wheel. The pivot spindle extends parallel to the X-ray screen as well as to the chute. The chute has a stop system to establish the testing position of the wheel on the chute and a clamping mechanism for immobilizing the wheel slid into the testing position. The X-ray tube is movable at least between a first operating position for the transillumination of the axial rim halves, and a second operating position for the transillumination of the wheel element support structure.

11 Claims, 6 Drawing Figures

VEHICLE WHEEL TESTING OR INSPECTION SYSTEMS

BACKGROUND OF THE INVENTION

The present invention relates to systems for X-ray testing or inspection of vehicle wheels which consist of a rim and an inner support structure, of the kind comprising an X-ray tube installed in a radiation-proof casing and a fixed X-ray screen with a post-positioned monitor, for complete transillumination of the wheel held by sections within the beam path of the X-ray tube, the axial rim halves and the inner support structure being transilluminated under rotation of the wheel into the momentary testing position, and a system for reception of the wheel fed in rim-down, for placing the same in the beam path as well as for ejection of the wheel element tested.

A known system for X-ray inspection of wheels of light metal for motor vehicles for detection of shrink holes, cracks and the like, comprises a gripper mechanism whereby a wheel is grasped on a feed belt, lifted off and placed in the system. To this end, the wheel which is to be grasped must be separated from the line of wheels arriving on a feed belt and commonly impinging on each other, and pre-centred. The wheel fed in is deposited in the testing area of the system and is taken over by a handling mechanism which places the wheel in the momentary partially sloping testing position and holds the same during transillumination. During the testing operation, only part of a peripheral section of the rim is tested, that is to say substantially the one half of the rim width in the one testing position and the other half of the rim width in another testing position, and in a third testing position of the wheel its inner support structure carrying the rim is transilluminated, that is to say equally in part or else totally so, depending on the diametrical dimension of the wheel element. The shadow picture of the wheel transilluminated which appears on the X-ray screen of the radioscopy appliance is transmitted to a monitor so that the wheel may be inspected visually for faults incurred during the casting or setting stages. After completion of the inspection, the wheel is again set down by the handling mechanism and picked up and removed by the gripper mechanism or another system, whereupon the gripper mechanism feeds the next wheel element into the device.

The said gripper mechanism inclusive of the devices for isolating and pre-centring the wheel element, the handling mechanism as well as—if applicable—the separate ejection device inclusive of all control systems for these devices, represent a considerable structure complexity with commensurate costs for production, operation and maintenance. Primarily however, these systems and devices require an expenditure of time for their actions, which must be evaluated as an idle period lost to the actual X-ray testing operation, whereby the total cycling period for testing a separate wheel element is increased considerably.

It is an object of the invention to improve systems of the kind referred to above, to the effect that the idle period of a testing cycle for a wheel are shortened substantially under simplification of the structure of the system.

SUMMARY OF THE INVENTION

To achieve this and other objects, the system according to the invention comprises a chute for the wheel, which chute is displaceable around a horizontal pivot spindle, and is pivotable into the appropriate positions for reception, immobilisation during inspection and for ejection of the wheel, the pivot spindle of said chute extending parallel to the X-ray screen as well as to the chute, and wherein said chute has a stop system for establishing the testing position of the wheel element on said chute and a clamping mechanism for locking the wheel slipped into the testing position, and wherein said X-ray tube is pivotable between a first operating position for the transillumination of the axial rim halves and a second operating position for the transillumination of the inner support structure of the wheel.

The said idle periods are shortened substantially as compared with prior art systems, since many of the parts enumerated above are partially omitted and complementarily simplified substantially, i.e. are combined into a single and uncomplicated mechanism which operates under utilisation of the force of gravity. The gripper mechanism for example is rendered superfluous by using a chute, the isolation and pre-centring of the wheel element which is to be tested, performed before being grasped by said mechanism, also being eliminated since the line of recumbent wheel elements arriving on the feed belt may advance the wheel element positioned farthest forward until it tips on to the chute under the action of gravity and thereupon slips into a predetermined position co-determining the testing position of the wheel. An uncomplicated clamping system of the chute then performs the immobilising of the wheel on the chute in this position, the chute thereupon merely being pivoted into the testing positions. After completion of the inspection of the wheel element, the chute is pivoted into a downwardly sloping oblique position, so that the wheel element inspected slips out of the device automatically under the action of gravity. The structure of the device in question is also simplified by application of a chute, which implies corresponding economic advantages.

In development of the system, the pivot spindle of the chute extends at right angles to the beam path of the X-ray tube and extends below the feed plane and above the discharge plane for the wheel, as well as close to the line passing at right angles through the centre of the X-ray screen. Short displacement paths only are thus required for the chute and the X-ray tube.

BRIEF DESCRIPTION OF THE DRAWINGS

In order that the invention may be more clearly understood, reference will now be made to the accompanying drawings which show one embodiment thereof by way of example only and in which.

DETAILED DESCRIPTION OF A PREFERRED EMBODIMENT

Figure 1:
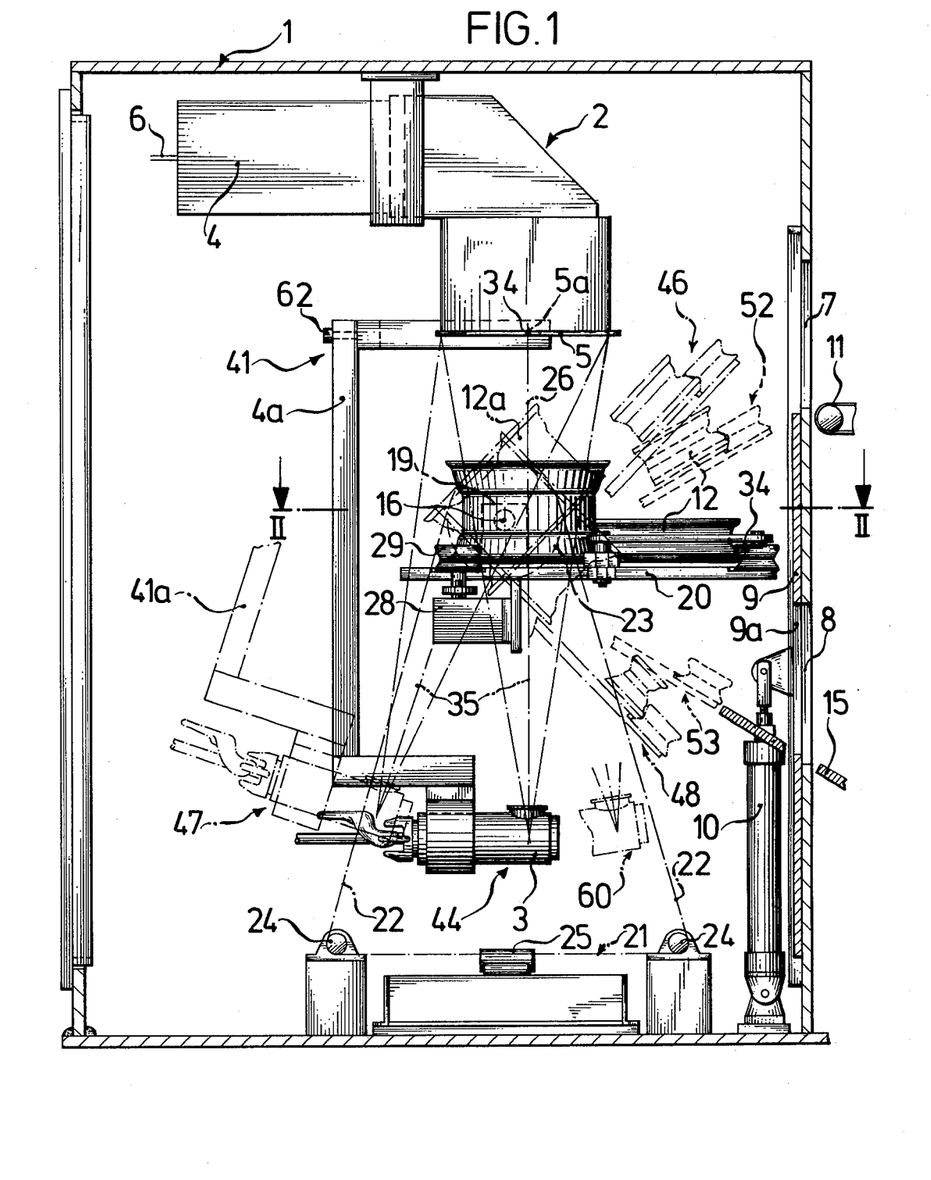
FIG. 1 shows a side view of a system in accordance with the invention.

Referring now to the drawings, according to the embodiment shown in FIG. 1, a radiation-proof casing 1 is provided, wherein is housed a radioscopy or fluoroscopy device 2 which comprises a lower X-ray tube 3 and a stationary upper reception system 4 which comprises an X-ray screen 5 aligned with the X-ray tube, which is irradiated by the X-rays. In conventional manner, the reception system 4 has a photographic camera (not illustrated) which is connected via a line 6 to a monitor (not shown) set up outside the casing 1, so that the shadow picture appearing on the X-ray screen of an object which is to be tested, may be inspected visually for faults. The casing 1 moreover has an upper ingress opening 7 and below the same an egress opening 8 for the object to be inspected, these openings being opened and closed by means of a bulkhead 9, the common bulkhead having at least one lower opening 9a which may be placed in congruency with the egress opening 8. The bulkhead or partition 9 is entrained in vertical direction by means of a pressure fluid cylinder 10 so that the casing 1 may be screened off completely against the transillumination radiation from the outside, during the transilluminating or testing operation.

Figure 2:
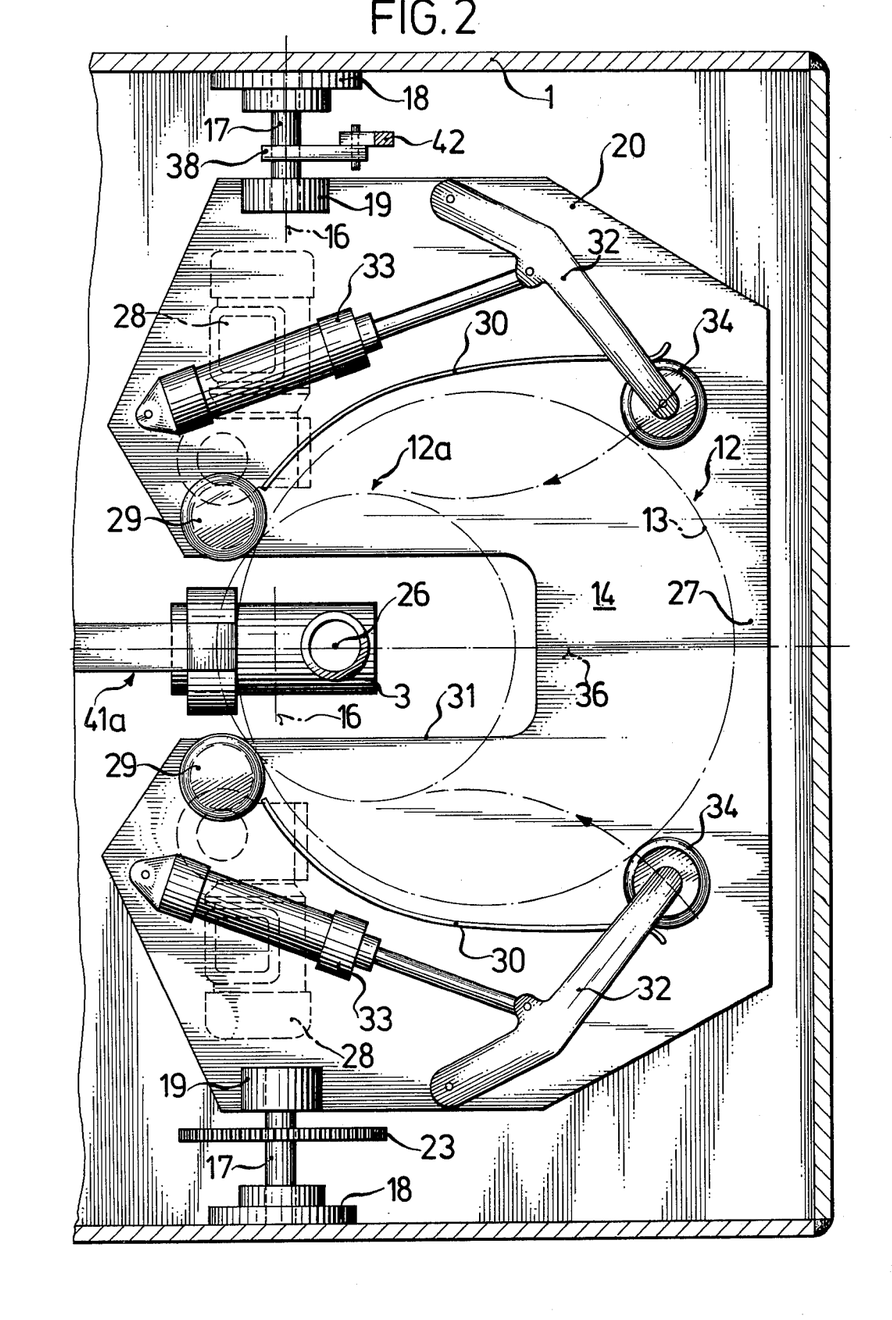
FIG. 2 shows a view corresponding to the line II—II in FIG. 1.

The upper ingress opening 7 of the casing 1 has allocated to it a feed belt 11 for the objects which are to be inspected, these objects consisting of wheel elements 12 in this case, which in conventional manner comprise the rim 13 and the inner support structure 14 (FIG. 2). The feed belt 11 extends substantially horizontally and successively conveys the wheel elements lying on it through the opening 7 of the casing 1, as hereinafter explained. Below the feed belt 11 is situated a discharge conveyor 15 which is allocated to the egress opening 8 of the casing 1 and extends obliquely. The wheels 12 to be inspected or tested travel slidingly from the casing 1 on to this discharge conveyor and are conveyed farther from said point in the manner required.

The casing 1 has situated in it a horizontal pivot spindle 16 which is formed by two lateral spindle elements 17 (FIG. 2), which are laterally secured to the casing 1 via bearers 18. The spindle elements 17 carry a flat plate 20 by way of bearers 19, said plate so being constructed as a chute for the wheel elements 12 to be inspected, being pivotable around the horizontal pivot spindle 16.

The pivoting of the chute 16 is performed by means of a laterally arranged traction drive mechanism 21, which for example comprises a driving chain 22 which runs over a sprocket 23 rotatorily arranged on a spindle element 17 as well as over two bottom deflecting sprockets 24 and is entrained in two opposed directions by means of a pressure-fluid-operated driving cylinder 25.

Figure 3:
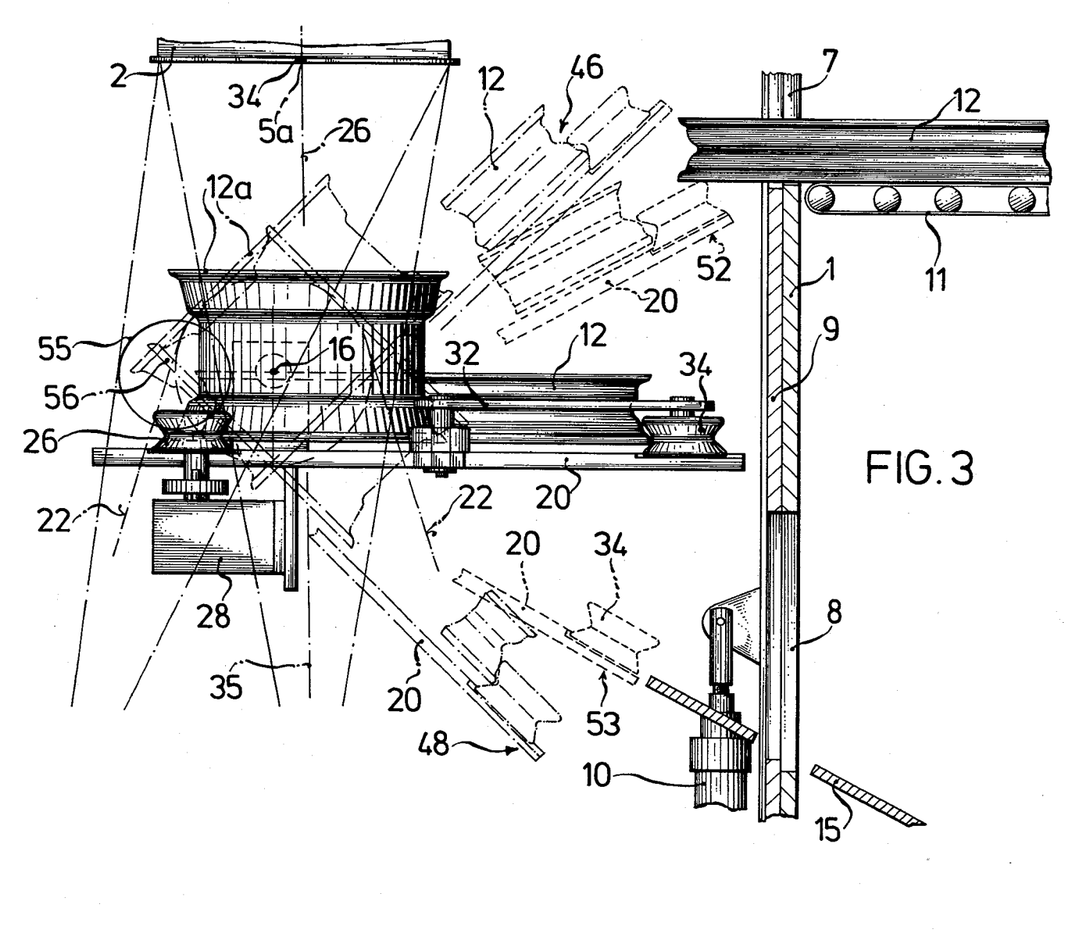
FIG. 3 shows a part of the side view of FIG. 1 to an enlarged scale.

The chute 20 serves the purpose of receiving one wheel 12 intended for inspection, in each case, of immobilising the same during the inspection by radioscopy, and of ejection of the wheel after inspection, to which end the chute is pivoted around the pivot spindle 16 into the corresponding positions by means of the drive 21, as will be apparent from the positions shown in FIGS. 1 and 3.

The pivot spindle 16 of the chute 20 extends parallel to the X-ray screen 5 as well as to the chute 20. In this embodiment, it extends at a particular spacing above the chute 20 and close to the line 26 at right angles extending through the centre 5a of the X-ray screen 5. With respect to this line at right angles, the pivot spindle extends in the rearwardly situated area of the chute 20, i.e. laterally of the line at right angles facing away from the feed and discharge section 27 of the chute. The pivot spindle is also so arranged, that it passes at right angles through the beam path of the X-ray tube 3 and extends below the plane of the feed belt 11 and above the plane of the discharge conveyor 15.

On its upper part, the chute 20 has a stop system for location of the testing position of the wheel 12 on the chute, which is most clearly shown in FIG. 2. This stop system comprises two mutually opposed rollers 29 each driven by a motor 28, against which slides the wheel 12 which is to be tested when it slips downwards obliquely on the chute 20. The rollers 29 establish the testing position of the wheel 12 on the chute 20.

To facilitate the sliding down of the wheel into this testing position, each roller 29 has allocated to it a wheel guide 30, the two guides extending divergently with respect to each other as far as the feed and discharge section 27 of the chute 20. For example, the guides 30 comprise plates of low height and are fixedly installed on the chute 20. For the sake of a clearer view, they are illustrated in FIG. 2 only.

As a modification, it is obviously possible for only one of the rollers 29 to be driven, or that both rollers 29 be freely rotatable and accordingly merely have an abutment function, whereas a separate motor-driven roller is incorporated for the rotary drive of the wheel which is to be tested.

The plane chute 20 is equipped with a central excision 31 moreover, which is open towards the rear chute section (FIG. 2) to provide unobstructed passage for the beam of the X-ray tube 3.

Furthermore, the chute 20 has a clamping device on its upper side for immobilisation of the wheel element 12 slid into the testing position on the chute, i.e. when the same has come to a stop against the stop rollers 29. This system comprises two mutually opposed levers 32 which are each pivotally displaced by means of a pressure fluid cylinder 33 and at their free ends have freely rotatable rollers 34 which grasp the wheel 12 by the lower flange in analogous manner to the stop rollers 19, as will be clearly seen in FIGS. 2 and 3 in particular.

The X-ray tube 3 may be pivoted into two operating positions to allow of transillumination of the whole wheel 12. In the embodiment illustrated, the pivot spindle 34 for the X-ray tube 3 extends within the plane of the X-ray screen 5 and parallel moreover to the pivot spindle 16 for the chute 20. Since the optical axis 35 of the X-ray tube 3 is identical with the said line 26 at right angles to the X-ray screen 5 in the one operating position of the X-ray tube (FIG. 1), the result is a vertical pivoting plane 36 of the X-ray tube 3, extending at right angles to the pivot spindle 16 of the chute 20.

A compact and uncomplicated structure of the proposed X-ray testing device, which furthermore allows of short displacement or pivoting paths, derives from the specified position and extension of the pivot spindles inclusive of the said pivoting plane.

The pivotal displacement of the X-ray tube 3 occurs synchronously with the pivotal displacement of the chute 20. To this end, a coupling linkage 37 is incorporated (FIG. 4) one lever 38 of which is co-rotatorily joined to the spindle element 17 and the other lever 39 of which is co-rotatorily joined to one of the two trunnions 40 of the mounting 41 for the X-ray tube 3. The two levers 39 are interconnected in articulated manner by a coupling rod 42. The coupling rod 42 is displaced in accordance with the direction in which the sprocket 23 is turned by the driving chain 22, so that the X-ray tube 3 is pivoted into two operating positions around the axis 34 according to the illustration in FIG. 4.

The illustration by a solid line of the coupling linkage 37 represents the horizontal testing position of the chute 20, as apparent for example from FIG. 1. At this setting, the coupling rod 42 is situated at position 43 according to FIG. 4, which has the result that the X-ray tube 3 is placed in its second operating position marked 44 in FIG. 1. At this setting of the X-ray tube, the chute 20 and thus the wheel element 12 immobilised thereon is or are situated in their second testing position. If the coupling rod 42 is placed in its position 45 according to FIG. 4, the chute 20 is pivoted into its topmost testing position which is shown dash-dotted in FIG. 1 and marked 46. At the same time, the X-ray tube 3 is pivoted synchronously into its first operating position, which is marked 47 in FIG. 1 and illustrated in dash-dot lines. When the chute 20 pivots into its lowest testing position, which is marked 48 in FIG. 1, the coupling rod 42 pivots into its position 49 according to FIG. 4, the X-ray tube 3 however having again regained its first operating position 47.

Figure 4:
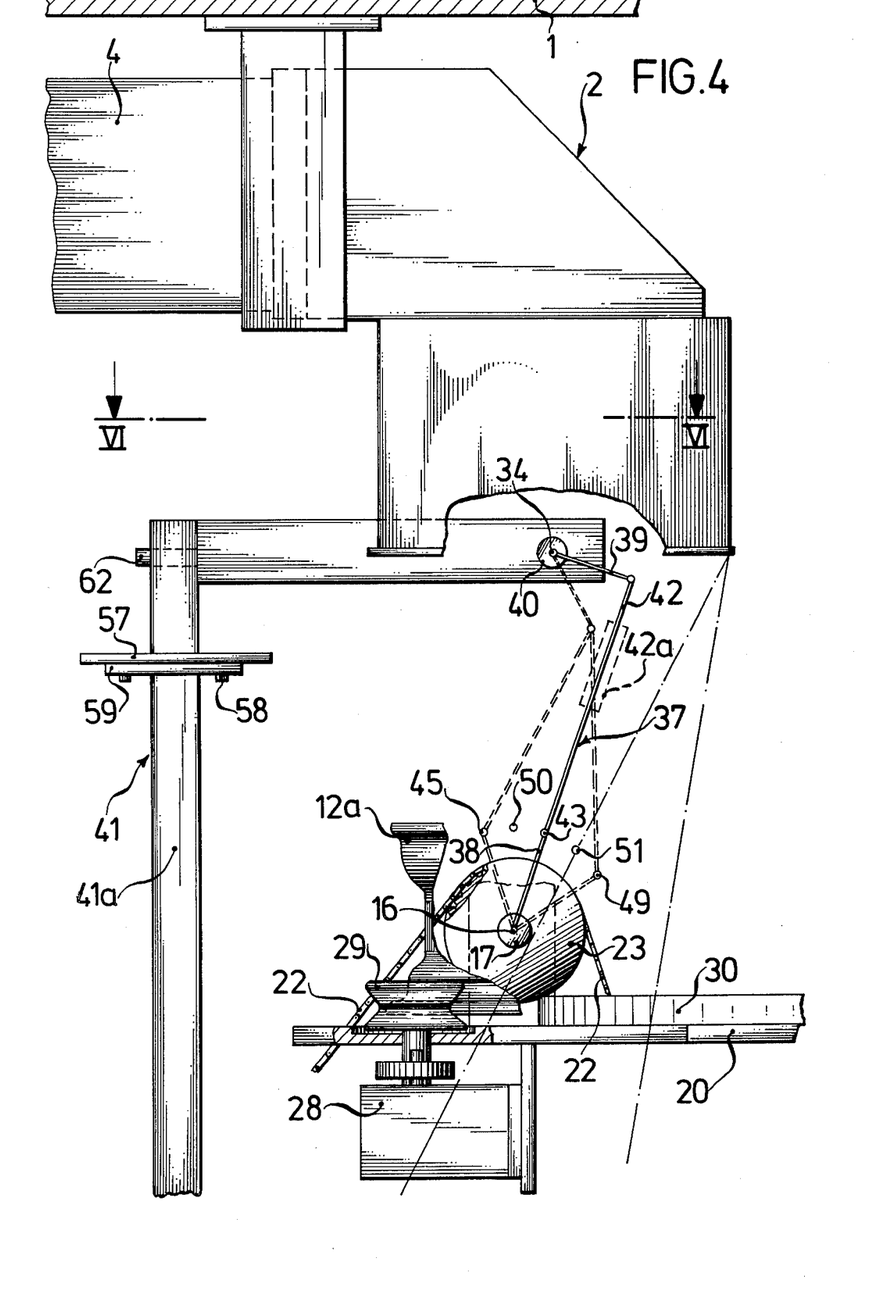
FIG. 4 shows another part of the side view of FIG. 1 to enlarged scale and in simplified form of illustration.

The intermediate settings 50 and 51 indicated in FIG. 4 denote intermediate positions of the coupling rod 42 and thus of the X-ray tube 3 when the chute 20 is in the reception or discharge position, which positions are denoted by 52 and 53 in FIG. 1. In these last-cited positions, the chute 20 is in each case aligned on the feed belt 11 or on the discharge conveyor 15.

Figure 5:
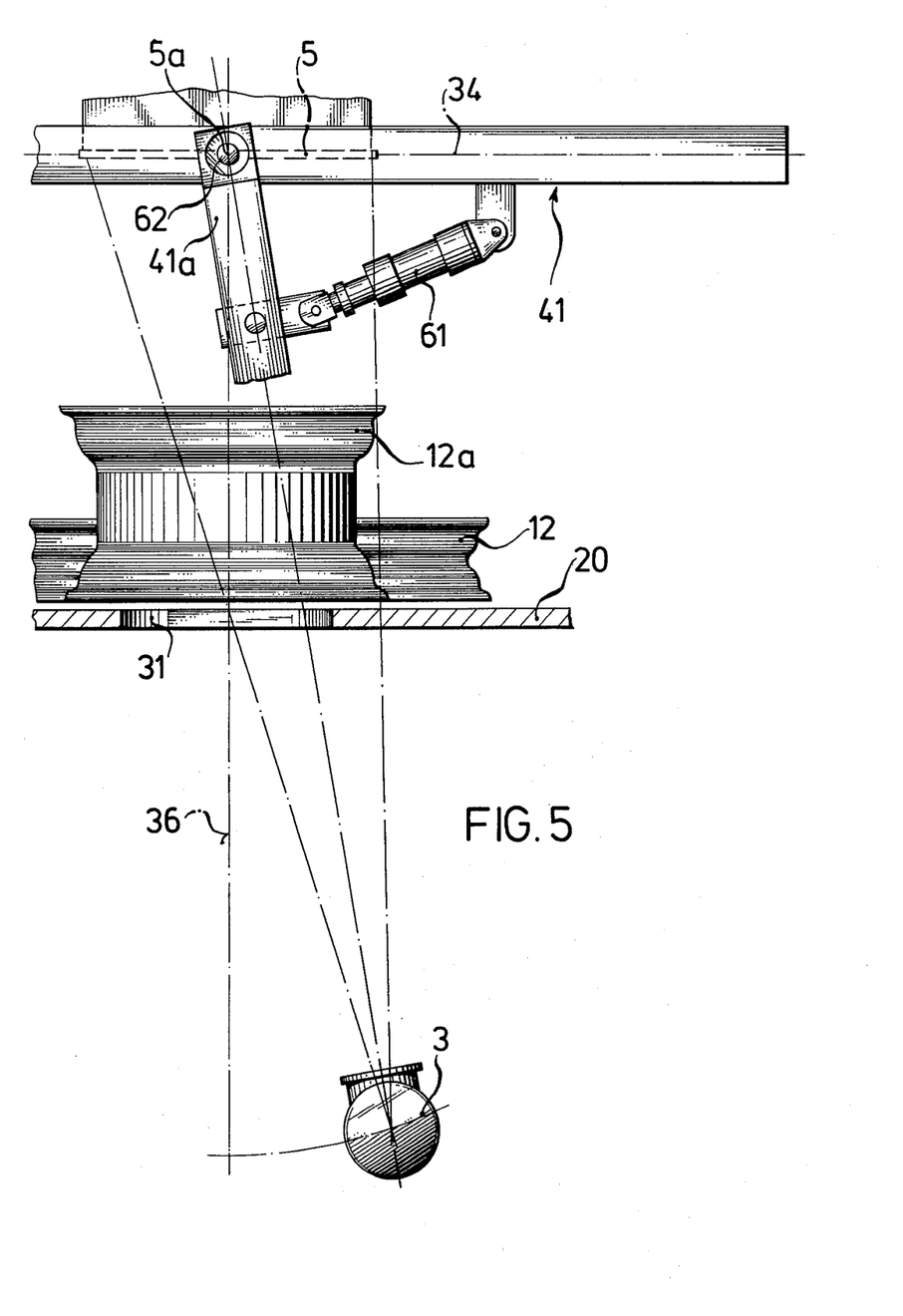
FIG. 5 shows a simplified view corresponding to the arrow V in FIG. 6.
Figure 6:
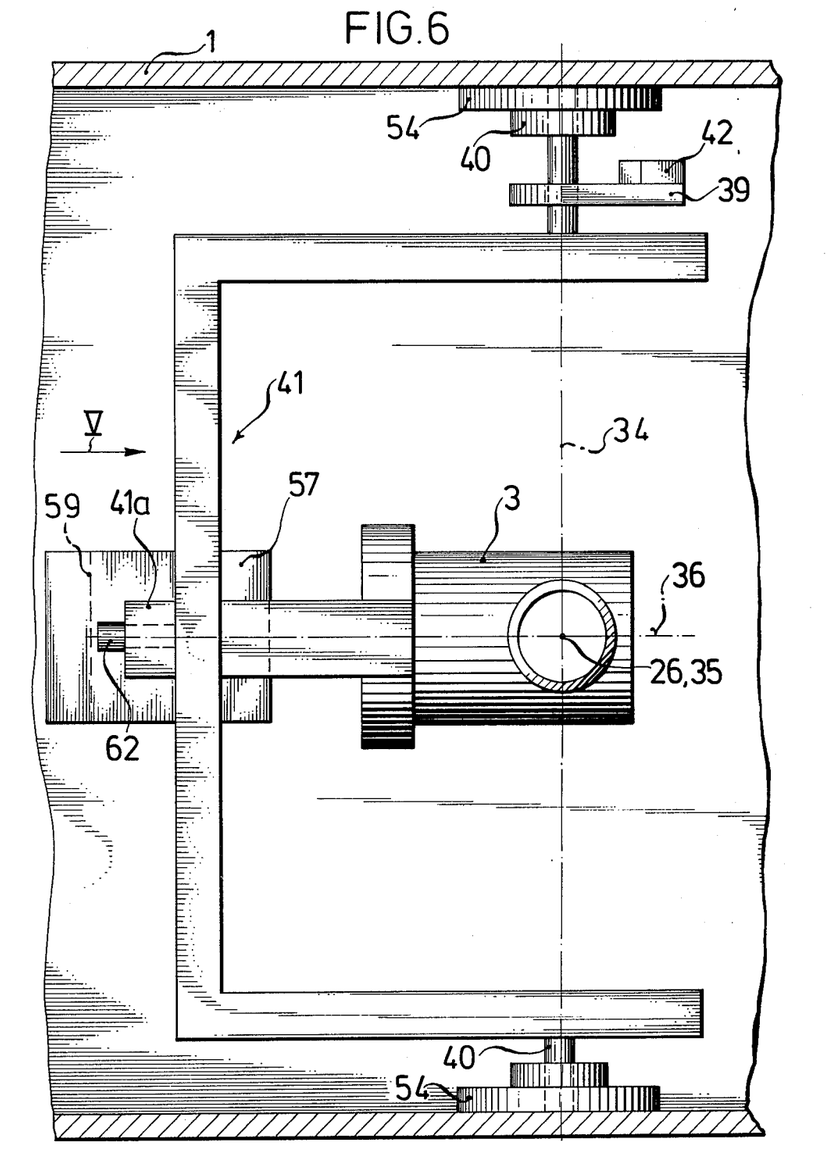
FIG. 6 shows a view corresponding to the line V—V in FIG. 4.

The manner in which the mounting 41 for the X-ray tube 3 is joined to the casing 1 via pivot bearings 54, is shown in FIG. 5.

The operation of the device so far described above will now be described.

FIG. 3 shows how a wheel 12 which is to be inspected or tested is advanced in the direction of the arrow on the feed belt 11. The empty chute 20 is in its reception position 52 at this time. When the wheel 12 has been pushed forward to the appropriate extent, it tips on the chute 20 under the action of gravity and slides downwards obliquely thereon until it impinges against the stop rollers 29, if applicable guided by the wheel guides 30. By actuation of the pressure fluid cylinders 33, the levers 32 cause the rollers 34 to bear against the lower flange of the wheel (FIG. 2), so that the wheel clamped between the rollers 29 and 34 is situated in its testing position on the chute. The chute is then pivoted farther upwards into the first testing position 46 and held fast thereat. By virtue of entrainment of the rollers 29, the wheel element 12 which has been raised a little from the chute 20, as shown in FIGS. 1 and 3, is placed in rotation and may then be transilluminated whilst the X-ray tube 3 is set at its first operating position 47. The area of the wheel rim which appears in the solid-line circle 55 in FIG. 3, is transilluminated and inspected in any event in this first testing position. This applies for wide rims, e.g. for rims 12a of private cars, as well as for narrow but in contradistinction diametrically larger rims or wheels 12, as equally apparent from FIG. 3.

When the rim portion in question has been wholly inspected peripherally, the chute 20 and thereby the wheel 12, 12a, is pivoted into the horizontal testing position. The X-ray tube 3 is then situated in its second operating position 44. The inner support structure 14 of the wheel 12 is then transilluminated and inspected. To this end, it will commonly be necessary for wheel elements of greater diameter, e.g. for motor cycle rims, equally to turn the rim or wheel element 12 once. This is not absolutely necessary in the case of private car rims 12a, as will be apparent from FIG. 3.

The chute 20 is thereupon pivoted downwards into its third testing position 48, the X-ray tube simultaneously having assumed its first operating position 47 again. The other half of the rim width denoted by 56 is then present in the circle 55 shown in FIG. 3. By rotating the wheel 12,12a, it is now also possible to transilluminate and inspect this axial rim portion.

After completion of this third transilluminating operation, the chute 20 is pivoted into its discharge position 53, which for example lies a little above the third testing position 48. The levers 32 are then opened again, so that the inpected wheel element slips off the chute 20 extending obliquely downwards under the action of gravity and by doing so reaches the sloping discharge conveyor 15 beyond the casing 1. Faulty rims may then be marked.

Upon changing from wide to narrow wheels and vice versa, it may be necessary for the X-ray tube 3 to be moved complementarily in translatory displacement at right angles to the pivot spindle 16 of the chute 20, so that the required rim area is properly set within the circle 55 for transillumination in any event. A displacement of this nature may be effected for example as shown in FIG. 4, by providing the mounting 41 with a fixed plate 57 which has joined to it by means of screws 58 a top plate 59 which carries the lower structure 41a of the mounting 41. The top plate 59 comprises longitudinal slots so that the structure 41 may be displaced in accordance with the double-headed arrow illustrated, after releasing the screws 58.

It may be necessary moreover to pivot the X-ray tube beyond its second operating position 44; this being the case if the total radial portion of the inner support structure of the wheel element cannot be covered entirely by means of the second operating position. This complementary pivotal displacement denoted by 60 in FIG. 1 is obtained by means of a pressure fluid cylinder 42a which is integrated into the coupling rod 42 as shown pecked in FIG. 4.

If the inner support structure of a wheel consisting of a light metal, e.g. aluminium, comprises a spoked pattern or the like, the X-ray tube 3 must be pivoted outwards from its first pivoting plane 36 to transilluminate the spoke pattern obliquely from the side. The construction according to FIG. 5 renders this possible. To this end, the lower structure 41a is pivotable by means of a pressure fluid cylinder 61 around the pin 62 of the mounting 41, so that the X-ray tube is pivotable within a vertical plane which extends at right angles to the first pivoting plane 36.

It is stated in the foregoing that the pivot spindle 16 extends above the plane working surface of the chute. It may obviously also coincide with the working surface or extend beneath the latter. In another embodiment, it is possible for the transillumination system 2 and the X-ray tube 3 to be interchanged in position, so that the system 2 is placed at the bottom and the X-ray tube at the top. A separate drive is incorporated in this case for the pivotal displacement of the X-ray tube 3.

Preferably the system described is used for the testing or inspection of light-metal rims, but it is also possible to test rims of steel and plastics material, as well as comparable elements.

I claim:

1. In a system for X-ray inspection of a motor vehicle wheel comprising a rim and an inner support structure, of the kind comprising an X-ray tube situated in a radiation-proof casing and a stationary X-ray screen with a post-positioned monitor, for totally transilluminating the wheel element held by sections in the beam path of the X-ray tube, the axial rim halves and the inner support structure being transilluminated in the corresponding testing or inspection position by rotation of the wheel, and a system for reception of the wheel which is fed in rim-down, for placing said wheel in the beam path as well as discharging the wheel after inspection, the invention which consists in that the system comprises a chute which is displaceable around a horizontal pivot spindle and intended for the wheel, said chute being pivotally displaceable into the positions in question for reception, immobilisation during inspection and discharge of the wheel, and wherein said pivot spindle of said chute extends parallel to said X-ray screen as well as to the working surface of said chute, said chute having a stop system for location of the inspection position of the wheel on said chute and a clamping mechanism for immobilising the wheel slipped into the inspection position, and wherein said X-ray tube is displaceable at least between a first operating position for transillumination of said axial rim halves and a second operating position for transillumination of said inner support structure of the wheel.

2. A system according to claim 1, wherein said pivot spindle of said chute passes at right angles through the beam path of said X-ray tube, and extends below the feed plane and above the discharge plane for the wheel as well as close to a line passing at right angles through the centre of said X-ray screen.

3. A system according to claim 2, wherein said pivot spindle is located laterally of said line at right angles, which faces away from the feed and discharge portion of said chute.

4. A system according to claim 1, wherein said X-ray tube is pivotally displaceable in a vertical plane coinciding with said right-angle line and extending at right angles to said pivot spindle of said chute for assuming its operating positions.

5. A system according to claim 4, wherein a pivot spindle for said X-ray tube extends within the X-ray screen plane and through said line at right angles to said X-ray screen.

6. A system according to claim 4, wherein said stop system comprises two mutually opposed rollers arranged symmetrically with respect to the pivoting plane of said X-ray tube, each said roller having allocated to it a wheel guide extending in the direction of the feed and discharge portion of said chute, both wheel guides extending divergently with respect to each other in the direction towards said discharge portion and at least one said roller being rotatable.

7. A system according to claim 1, wherein a traction mechanism drive effective in two directions is incorporated for pivotal displacement of said chute.

8. A system according to claim 1, wherein a coupling linkage is incorporated for pivotal displacement of said X-ray tube, said coupling linkage being arranged to the pivotal displacement of said chute to said X-ray tube.

9. A system according to claim 1, wherein said chute comprises a flat plate which is provided with a rearwardly open excision for free passage of the beam of said X-ray tube.

10. A system according to claim 4, wherein said X-ray tube is movable complementarily in translatory displacement at right angles to said pivot spindle of said chute within its pivoting plane.

11. A system according to claim 4, wherein said X-ray tube is pivotally displaceable with respect to its first pivoting plane in another plane which extends at right angles and vertically to said first plane.

* * * * *